(12) United States Patent
Rogers et al.

(10) Patent No.: US 7,544,824 B2
(45) Date of Patent: Jun. 9, 2009

(54) SHEA BUTTER ALKOXYLATES

(75) Inventors: Steven Rogers, Yardley, PA (US); Anthony O'Lenick, Jr., Dacula, GA (US)

(73) Assignee: Vertellus Specialties, Inc., Indianapolis, IN (US)

( * ) Notice: Subject to any disclaimer, the term of this patent is extended or adjusted under 35 U.S.C. 154(b) by 123 days.

(21) Appl. No.: 11/347,272

(22) Filed: Feb. 6, 2006

(65) Prior Publication Data

US 2007/0184009 A1    Aug. 9, 2007

(51) Int. Cl.
*C07C 57/00* (2006.01)
(52) U.S. Cl. ..................................................... 554/227
(58) Field of Classification Search ....................... None
See application file for complete search history.

*Primary Examiner*—Deborah D Carr
(74) *Attorney, Agent, or Firm*—Louis C. Paul

(57) ABSTRACT

Novel alkoxylates prepared by the reaction of mild-processed shea butter (MPSB) with ethylene oxide, propylene oxide or mixtures thereof. These compounds are useful as cosmetic and personal care ingredients, allowing for the delivery of highly desirable active ingredients present in MPSB, including natural antioxidants, in a water-soluble form that is substantive to the skin and hair.

6 Claims, No Drawings

SHEA BUTTER ALKOXYLATES

CROSS-REFERENCE TO RELATED APPLICATIONS

Not applicable.

STATEMENT REGARDING FEDERALLY-SPONSORED RESEARCH OR DEVELOPMENT

Not applicable.

FIELD OF THE INVENTION

The present invention relates to novel mild-processed shea butter alkoxylates prepared by the reaction of mild-processed shea butter (MPSB) with ethylene oxide, propylene oxide or mixtures thereof. These compounds are useful as cosmetic and personal care ingredients, allowing for the delivery of highly desirable active ingredients present in MPSB, including natural antioxidants, in a water-soluble form that is substantive to the skin and hair.

BACKGROUND OF THE INVENTION

Shea Butter is a butter extracted from the kernel of *Butrospermum parkii*. This plant, also referred to as *Vitellaria paradoxa*, is native to Africa. The term butter describes a material that is a solid at room temperature, but melts at about 40° C. Chemically, the butter is a triglyceride conforming to the following structure

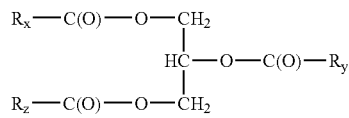

wherein $R_x$, $R_y$ and $R_z$ each have one of the following compositions:

| R Group | Common Name | Range (%) | Typical (%) |
|---|---|---|---|
| $C_{11}H_{23}$ | Lauryl | 0.1-2.0 | 0.2 |
| $C_{13}H_{27}$ | Myristyl | 0.5-2.0 | 1.0 |
| $C_{15}H_{31}$ | Cetyl | 2.0-6.0 | 4.0 |
| $C_{17}H_{35}$ | Stearyl | 25.0-50.0 | 35.0 |
| $C_{17}H_{33}$ | Oleyl | 40.0-60.0 | 59.0 |
| $C_{17}H_{31}$ | Linoleyl | 0.5-1.0 | 0.8 |

The average composition of $R_y$ is different than $R_x$ and $R_z$, the latter two being similar. The $R_y$ moiety contains predominantly the unsaturated $C_{18}$ group (oleyl) while $R_x$ and $R_z$ contain predominantly the saturated $C_{18}$ group (stearyl). Differences between internal ($R_y$) and terminal ($R_x$, $R_z$) substitution are seen in natural products, but not in synthetic molecules produced in the laboratory.

The high levels of stearyl and oleyl groups in mild-processed shea butter and its alkoxylate derivatives make them of particular interest in the personal care industry. While other raw materials used in personal care products have these species, the compounds of the present invention have significantly high concentrations of unsaponifiables, which posses highly desired antioxidant, ultra-violet radiation protection, and free-radical scavenging properties. MPSB alkoxylates of the present invention typically contain from about 5% to about 15% by weight of unsaponifiables. In contrast, other butters commonly used in personal care products have less than 2% unsaponifiables. For example, coca butter (from *Theobroma cacao*) averages 0.4% unsaponifiables and Illipe butter (from *Shorea stenoptera*) averages 1.1%.

As described in greater detail below, the novel mild-processed shea butter alkoxylates of the present invention are produced by an ethenification reaction of MPSB with ethylene oxide, propylene oxide or mixtures thereof under specific mild-processing conditions. By "mild processed" is meant processes that do not remove or otherwise diminish the amount or potency of active ingredients, particularly highly desired unsaponifiables. In the present invention, mild processing is employed both at the time of harvesting and initial extraction (creating mild-processed shea butter) and during subsequent preparation of its alkoxylate derivatives. These processes result in materials containing unexpectedly high amounts unsaponifiables, notably antioxidants.

Polyoxyethylene glycol (PEG)/Polyoxypropylene glycol (PPG) esters are described in the prior art. U.S. Pat. No. 5,917,070 teaches polyoxyalkylene glycol esters prepared by the reaction of polyoxyalkylene glycol with meadowfoam oil as a triglyceride, as a fatty acid or as a methyl ester. The meadowfoam PEG/PPG esters are described as having good oxidative stability which is attributed to the specific carbon chain distribution of meadowfoam oil. These prior art compounds differ, however, from the alkoxylated mild-processed shea butters of the present invention in which ethylene oxide, propylene oxide and mixtures are inserted into mild-processed shea butter through an ethenification reaction.

Ethoxylated shea butter is listed in the International Dictionary of Cosmetic Ingredients (10$^{th}$ Edition), published by the Cosmetics, Toiletries and Fragrance Association. Ethoxylated shea butter having about 75 moles of ethylene oxide per mole of glyceride is commercially available under the tradename Lipex™ 102 E75 from Karlshamns AB (Karlshamn, Sweeden). This material is extracted with hydrocarbon solvents. Ethoxylated shea butter is also commercially available form Oils By Nature (Cleveland, Ohio) and KIC Chemicals, Inc. (Armonk, N.Y.).

The novel alkoxylates of the present invention are water-soluble emollients that not only not only condition and soften skin and hair, but also deliver antioxidants (present in the unsaponifiable fraction of mild-processed shea butter) in a heretofore unachievable manner.

SUMMARY OF THE INVENTION

The compounds of the present invention are mild-processed shea butter alkoxylates produced by an ethenification reaction conducted under mild-processing conditions of mild-processed shea butter with ethylene oxide, propylene oxide and mixtures thereof. The novel alkoxylates of the present invention are rich in unsaponifiables, including antioxidants.

DETAILED DESCRIPTION OF THE INVENTION

The present invention relates to a novel class of alkoxylates made by reacting mild-processed shea butter with ethylene oxide, propylene oxide and mixtures thereof under specific mild-processing conditions. Another aspect of the present invention relates to a process for using these compounds in personal care applications. Mild processing is employed both at the time of harvesting and initial extraction and during subsequent preparation of alkoxylate derivatives. In so doing, materials containing unexpectedly high amounts of active ingredients, particularly highly desired unsaponifiables, are produced.

MPSB alkoxylates of the present invention conform to the following structure:

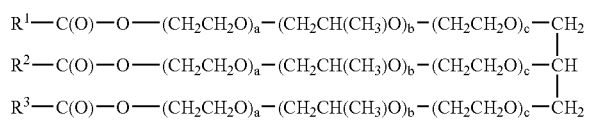

(i) wherein $R^1$, $R^2$, $R^3$ are each derived from mild-processed shea butter
which comprises
from about 0.1% to about 2.0% by weight $C_{11}H_{23}$;
from about 0.5% to about 2.0% by weight $C_{13}H_{27}$;
from about 2.0% to about 6.0% by weight $C_{15}H_{31}$;
from about 25% to about 50% by weight $C_{17}H_{35}$;
from about 40% to about 60.0% by weight $C_{17}H_{33}$; and
(ii) a, b and c are independently integers ranging from 1 to 20.

Another aspect of the present invention is a process for delivering antioxidants to the skin and hair by applying thereto a finished topical product comprising an effective amount of an alkoxylate made by an ethenification reaction of MPSB and ethylene oxide, propylene oxide and mixtures thereof that conforms to the following structure:

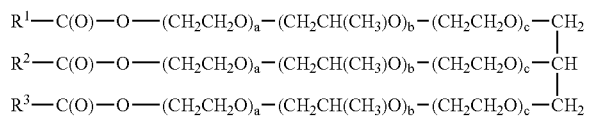

(i) wherein $R^1$, $R^2$, $R^3$ are each derived from mild-processed shea butter
which comprises
from about 0.1% to about 2.0% by weight $C_{11}H_{23}$;
from about 0.5% to about 2.0% by weight $C_{13}H_{27}$;
from about 2.0% to about 6.0% by weight $C_{15}H_{31}$;
from about 25% to about 50% by weight $C_{17}H_{35}$;
from about 40% to about 60.0% by weight $C_{17}H_{33}$; and
(ii) a, b and c are independently integers ranging from 1 to 20.

By "finished topical product" is meant a cream, lotion, gel, foam, ointment, paste, emulsion, suspension, dispersion, solution, or similar topically-applied carrier or delivery system known to those of skill in the art.

Mild-processed shea butter is made using a hydrocarbon-free solvent system and its alkoxylate derivatives of the present invention are made under mild processing conditions. At the time of harvesting and initial extraction ground-up kernels are boiled in water under mild conditions described in the examples below. The oil phase is then separated from the water phase by decanting. This process provides a yellow solid wax rich in unsaponifiables. By wax is meant a material obtained by boiling in water under ambient conditions, decanted and filtered.

The mild processing of the present invention may be contrasted with separation using solvents and high temperature treatment with high pressure steam. While the latter processes result in what some may describe as a "more pure" triglyceride, unsaponifiables, and the benefits derived therefrom, are lost. Vacuum distillation which strips off the desirable components is also to be avoided in processing MPSB of the present invention. By processing shea butter under mild conditions, materials comprising from about 5% to about 15% by weight of unsaponifiables can be produced.

Sterols comprise about 20% of the unsaponifiables. More particularly, the sterols comprise: cholesterol (from about 1% to about 3%); alpha-spinasterol (from about 1% to about 4%); delta-7-stigmasterol (from about 40% to about 44%); delta-7-avenasterol (from about 38% to about 41%). The remaining constituents of the unsaponifiables (about 80%) include other highly desirable active compounds including tocopherol, karitin, cinamic acid esters, alpha and beta amyrin and phenolics.

Phenolic compounds are natural products composed of one or more aromatic benzene rings with one or more hydroxyl group. They are a class of natural products that possess antioxidant and free radical scavenging properties. Among the phenolics in the unsaponifiables of mild-processed shea butter include gallic acid, gallocatchin, catechin, epigallocatechin gallate, epicatechin, gallocatechin gallate, gallocatechin gallate and quercetin.

Ethylene oxide is an item of commerce that conforms to the following structure:

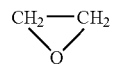

Propylene oxide is an item of commerce conforming to the following structure:

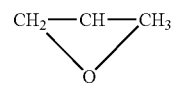

The following examples are further illustrative of the present invention. The components and specific ingredients are presented as being typical, and various modifications can be derived in view of the foregoing disclosure within the scope of the invention. All percentages, ratios and proportions herein are by weight, unless otherwise specified. All temperatures are in degrees Celsius unless otherwise specified.

EXAMPLES

The starting MPSB is made according to following procedure: 400.0 grams of the nut form the shea butter tree are cracked into small pieces and placed into a one-liter vat of water. The water is then heated to 100° C. As the temperature increases, an oil phase develops on the surface of the water. The temperature is held for about 2 hours, after which the oil is decanted and passed through filter paper. The resulting butter is mild-processed shea butter according to the present invention. It is rich in unsaponifiable (from about 7% to about 15% by weight) and may be used in making the MPSB dimethicone copolyol derivatives, including MPSB DMC esters, of the present invention.

The specified grams of the ethylene oxide (EO) and/or propylene oxide (PO) in Examples 1-7 are added to MPSB in the presence of 0.1% KOH based on the total weight of mild-processed shea butter and the alkylene oxide(s). The reaction mass is heated to, and held at, about 150° C. for about ## hours.

| Example | EO (grams) | PO (grams) | EO (grams) |
|---------|------------|------------|------------|
| 1 | 44 | 0 | 0 |
| 2 | 0 | 59 | 0 |
| 3 | 880 | 1180 | 880 |
| 4 | 0 | 590 | 440 |
| 5 | 440 | 0 | 0 |
| 6 | 250 | 59 | 200 |
| 7 | 44 | 590 | 0 |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A mild-processed shea butter alkoxylate conforming to the structure:

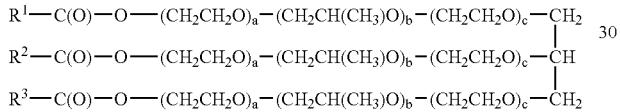

(i) wherein $R^1$, $R^2$, $R^3$ are each derived from mild-processed shea butter which comprises from about 0.1% to about 2.0% by weight $C_{11}H_{23}$;
from about 0.5% to about 2.0% by weight $C_{13}H_{27}$;
from about 2.0% to about 6.0% by weight $C_{15}H_{31}$;
from about 25% to about 50% by weight $C_{17}H_{35}$;
from about 40% to about 60.0% by weight $C_{17}H_{33}$; and (ii) a, b and c are independently integers ranging from 1 to 20.

2. A mild-processed shea butter alkoxylate of claim 1, where a is 10, b is 10 and c is 10.

3. A mild-processed shea butter alkoxylate of claim 1, where a is 5, b is 2 and c is 10.

4. A process for delivering antioxidants to the hair and skin by applying thereto a finished topical product comprising an effective concentration of a mild-processed shea butter alkoxylate conforming to the structure:

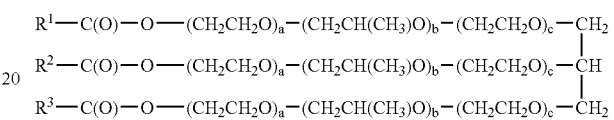

(i) wherein $R^1$, $R^2$, $R^3$ are each derived from mild-processed shea butter which comprises from about 0.1% to about 2.0% by weight $C_{11}H_{23}$;
from about 0.5% to about 2.0% by weight $C_{13}H_{27}$;
from about 2.0% to about 6.0% by weight $C_{15}H_{31}$;
from about 25% to about 50% by weight $C_{17}H_{35}$;
from about 40% to about 60.0% by weight $C_{17}H_{33}$; and (iii) a, b and c are independently integers ranging from 1 to 20.

5. A process of claim 4, where a is 10, b is 10 and c is 10.

6. A process of claim 4, where a is 5, b is 2 and c is 10.

* * * * *